United States Patent
Koss (10) Patent No.: US 10,285,818 B2
(45) Date of Patent: May 14, 2019

(54) APPARATUS, KIT, AND METHOD FOR PERCUTANEOUS INTERVERTEBRAL DISC RESTORATION

(71) Applicant: Scott A. Koss, Delafield, WI (US)

(72) Inventor: Scott A. Koss, Delafield, WI (US)

(73) Assignee: SYMBIOMEDIK, LLC, Delafield, WI (US)

( * ) Notice: Subject to any disclaimer, the term of this patent is extended or adjusted under 35 U.S.C. 154(b) by 535 days.

(21) Appl. No.: 14/141,125

(22) Filed: Dec. 26, 2013

(65) Prior Publication Data

US 2014/0180415 A1  Jun. 26, 2014

Related U.S. Application Data

(60) Provisional application No. 61/745,895, filed on Dec. 26, 2012.

(51) Int. Cl.
*A61F 2/44* (2006.01)
*A61F 2/46* (2006.01)
*A61F 2/30* (2006.01)

(52) U.S. Cl.
CPC ............ *A61F 2/441* (2013.01); *A61F 2/4611* (2013.01); *A61F 2002/3008* (2013.01); *A61F 2002/30092* (2013.01); *A61F 2002/444* (2013.01)

(58) Field of Classification Search
CPC .. A61F 2/44; A61F 2/441; A61F 2/442; A61F 2/46; A61F 2/4601; A61F 2/4603;
(Continued)

(56) References Cited

U.S. PATENT DOCUMENTS 3,875,595 A  4/1975  Froning
4,772,287 A  9/1988  Ray et al.
(Continued)

FOREIGN PATENT DOCUMENTS

EP       1229873      1/2004
WO    2003039412      5/2003
(Continued)

OTHER PUBLICATIONS

PCT Search Report and Written Opinion for International Application No. PCT/US2013/077845 dated Mar. 19, 2014.
(Continued)

*Primary Examiner* — Lynnsy M Summitt
(74) *Attorney, Agent, or Firm* — Michael Best & Friedrich LLP (57) ABSTRACT

An assembly for replacing a vertebral disc. The assembly includes an implant and a device for positioning the implant between two adjacent vertebrae. The implant includes a body having an internal compartment enclosed by an outer wall, and an endoskeleton coupled to the body. The device includes a cannula, a container coupled to the cannula, the container having a first end and a second end, a plunger threadingly coupled to the cannula and to the first end of the container, and a conduit coupled to the second end of the container and in fluid communication with the body of the implant. The implant is positioned within the cannula in an undeployed state and is deployed within a vertebral disc to receive a biological fluid in a second state.

14 Claims, 9 Drawing Sheets

(58) Field of Classification Search
CPC .............. A61F 2/4611; A61F 2002/442; A61F 2002/4475; A61F 2002/4495; A61F 2002/46; A61F 2002/4601; A61F 2002/4603; A61F 2002/4627; A61F 2002/444

See application file for complete search history.

(56) References Cited

U.S. PATENT DOCUMENTS

| | | | |
|---|---|---|---|
| 5,108,404 | A | 4/1992 | Scholten et al. |
| 5,562,736 | A | 10/1996 | Ray et al. |
| 5,571,189 | A | 11/1996 | Kuslich |
| 5,645,597 | A | 7/1997 | Krapiva |
| 6,306,177 | B1 | 10/2001 | Felt et al. |
| 6,383,190 | B1 * | 5/2002 | Preissman .......... A61B 17/8819 606/92 |
| 6,582,467 | B1 * | 6/2003 | Teitelbaum ........ A61B 17/1615 623/17.11 |
| 6,733,505 | B2 | 5/2004 | Li |
| 6,733,533 | B1 | 5/2004 | Lozier |
| 6,740,093 | B2 * | 5/2004 | Hochschuler ...... A61B 17/7097 606/94 |
| 6,764,514 | B1 | 7/2004 | Li et al. |
| 6,852,095 | B1 | 2/2005 | Ray |
| 7,081,120 | B2 | 7/2006 | Li et al. |
| 7,128,746 | B2 | 10/2006 | Singer et al. |
| 7,214,245 | B1 | 5/2007 | Marcolongo et al. |
| 7,258,700 | B2 | 8/2007 | Lambrecht et al. |
| 7,267,687 | B2 | 9/2007 | McGuckin, Jr. |
| 7,488,337 | B2 * | 2/2009 | Saab ................ A61B 17/8855 604/96.01 |
| 7,520,900 | B2 * | 4/2009 | Trieu ...................... A61F 2/441 623/17.16 |
| 7,628,800 | B2 * | 12/2009 | Sherman .................. A61F 2/44 606/279 |
| 7,641,691 | B2 | 1/2010 | Lotz et al. |
| 7,699,894 | B2 | 4/2010 | O'Neil et al. |
| 7,799,078 | B2 * | 9/2010 | Embry ............... A61B 17/7097 606/94 |
| 7,947,080 | B2 | 5/2011 | Ferree |
| 7,976,578 | B2 * | 7/2011 | Marvel .............. A61F 2/30756 623/14.12 |
| 8,038,682 | B2 | 10/2011 | McGill et al. |
| 8,287,595 | B2 * | 10/2012 | Vresilovic .............. A61L 27/52 606/279 |
| 8,292,961 | B2 * | 10/2012 | Osman ............... A61B 17/7097 623/17.12 |
| 8,529,628 | B2 * | 9/2013 | Marino ............. A61B 17/7098 623/17.11 |
| 2002/0077701 | A1 | 6/2002 | Kuslich |
| 2002/0147497 | A1 | 10/2002 | Belef et al. |
| 2004/0030345 | A1 | 2/2004 | Aurin et al. |
| 2004/0167625 | A1 | 8/2004 | Beyar et al. |
| 2005/0043796 | A1 | 2/2005 | Grant et al. |
| 2005/0143826 | A1 | 6/2005 | Zucherman et al. |
| 2005/0245938 | A1 * | 11/2005 | Kochan .............. A61B 17/7097 606/92 |
| 2005/0261781 | A1 | 11/2005 | Sennett et al. |
| 2006/0079905 | A1 * | 4/2006 | Beyar ................ A61B 17/7095 606/76 |
| 2006/0149380 | A1 | 7/2006 | Lotz et al. |
| 2006/0247657 | A1 | 11/2006 | Trieu |
| 2006/0293751 | A1 * | 12/2006 | Lotz ....................... A61F 2/441 623/17.12 |
| 2007/0055201 | A1 * | 3/2007 | Seto .................... A61B 17/1617 604/96.01 |
| 2007/0088436 | A1 | 4/2007 | Parsons et al. |
| 2007/0173943 | A1 | 7/2007 | Dulak et al. |
| 2007/0219490 | A1 * | 9/2007 | Pepper .................. A61L 29/085 604/103.13 |
| 2008/0009823 | A1 * | 1/2008 | McKay .............. A61B 17/7044 604/500 |
| 2008/0007135 | A1 | 3/2008 | Greenhalgh et al. |
| 2008/0091167 | A1 | 4/2008 | Trieu |
| 2008/0103596 | A1 | 5/2008 | Shikinami et al. |
| 2008/0140201 | A1 | 6/2008 | Stad et al. |
| 2008/0249604 | A1 | 10/2008 | Donovan et al. |
| 2009/0069850 | A1 * | 3/2009 | Fuerderer .......... A61B 17/7097 606/279 |
| 2009/0076610 | A1 | 3/2009 | Afzal |
| 2009/0131939 | A1 * | 5/2009 | Ahrens ................. A61F 2/4405 606/80 |
| 2009/0149958 | A1 * | 6/2009 | Prewett .................. B29C 70/24 623/17.16 |
| 2009/0254186 | A1 | 10/2009 | Tornier et al. |
| 2010/0076481 | A1 | 3/2010 | Stephens et al. |
| 2010/0145454 | A1 | 6/2010 | Hoffman |
| 2010/0168859 | A1 | 7/2010 | Wardlaw |
| 2010/0168864 | A1 * | 7/2010 | White ............... A61B 17/06114 623/18.11 |
| 2011/0046737 | A1 | 2/2011 | Teisen |
| 2011/0184349 | A1 | 7/2011 | McKay |
| 2011/0270399 | A1 | 11/2011 | Yurek et al. |

FOREIGN PATENT DOCUMENTS

| | | | |
|---|---|---|---|
| WO | 2004064673 | | 8/2004 |
| WO | 2006115956 | | 11/2006 |
| WO | WO 2012064473 A1 * | 5/2012 | ............. A61F 2/441 |

OTHER PUBLICATIONS

European Supplementary Search Report for EP Application No. 13867389.2 dated Aug. 22, 2016.

International Search Report with Written Opinion for related Application No. PCT/US18/13578 dated Mar. 13, 2018 (16 Pages).

* cited by examiner

FIG. 1A

Structures of the Spine

FIG. 1B

Section of the Spine

APPARATUS, KIT, AND METHOD FOR PERCUTANEOUS INTERVERTEBRAL DISC RESTORATION

FIELD OF THE INVENTION

The present invention relates to devices, kits, and methods for percutaneous intervertebral disc restoration with a nucleus pulposus implant.

BACKGROUND OF THE INVENTION

The human spine is made up of consecutively aligned vertebral bodies. Each pair of adjacent vertebral bodies is separated and supported by an intervertebral disc positioned therebetween. Each intervertebral disc includes an annulus fibrosus which surrounds a central nucleus pulposus. Healthy discs are capable of carrying a tremendous load.

The annulus fibrosis is made up of both Type 1 and Type 2 collagen having a lamellar formation and an alternating fiber orientation. The annulus fibrosis provides axial support with the help of the nucleus pulposus, which maintains the vertical orientation of the annulus fibrosis.

Back pain affects millions of people in the United States and around the world. Back pain has a variety of causes. One of the most common causes of back pain is disc degeneration. Aging causes the disc to begin to desiccate or lose water. As the nucleus changes shape and loses height, the annulus begins to weaken as a result of increased load forces. A weakened annulus is susceptible to annular failure, which results in tears, bulges, and herniations of the annulus. Weakening of the components of the disc eventually causes increased deformation of the disc, which further weakens the nucleus. This cycle of deterioration encourages end plate degeneration and facet hypertrophy, and ultimately back pain escalation.

Currently, there are several ways to manage the pain associated with disc degeneration. The most conservative approach is to use pain medications such as NSAIDS, steroid packs, and narcotics. Most often, these medications are administered in conjunction with both physical and massage therapy. An alternative and preferred conservative approach is to inject epidural steroids. Back pain can also be mitigated by a minimally invasive procedure known as intradiscal electrothermal therapy (IDET). IDET includes thermal ablation of the inner annulus. The thermal energy associated with IDET repairs collagen and ultimately stimulates collagen synthesis. While IDET results in statistically significant pain and disability improvement, is more effective on patients with greater disability at the onset of treatment and therefore is a worthwhile intervention for some highly select patients. More aggressive treatment of back pain includes one of several lumbar spine surgeries such as a microdiscectomy, a fusion, a disc annuloplasty, a laminectomy, or a foraminotomy. While surgery is a viable option as a solution for back pain, it has inherent associated surgical risks, in-hospital recovery, significant failure rate, and an expensive process. As a result, better solutions for reducing or eliminating back pain are desirable.

SUMMARY OF THE INVENTION

One solution is to treat back pain with a more permanent solution without the surgical risks, prolonged recovery time, and expense incurred through surgery. Therefore, one embodiment of the present invention is a device and method for replacement of the nucleus pulposus. Replacing the nucleus pulposus restores strength to the central disc and restores height of the annulus for improved structural integrity of the spine such that the cycle of back pain described above is not perpetuated.

In one embodiment, the present invention provides a medical device or instrument including a cannula and a syringe assembly for inserting an implant.

In another embodiment, the present invention provides an implant, which includes a nuclear implant having a body and a port, has a first state and a second state. The implant further includes a flexible material and is coupled to the syringe assembly. When the nuclear implant is in the first state, the body is empty and when the nuclear implant is in the second state, the flexible material is inserted into the body of the nuclear implant through the port such that the flexible material is contained within the body of the nuclear implant.

In yet another embodiment, the present invention provides a method for inserting the implant between adjacent vertebral bodies. The method includes coupling a deformable nuclear implant to a needle on a distal end of a syringe, the syringe containing a flexible material, and then inserting the syringe into a cannula. The method further includes inserting the cannula into a space between adjacent vertebrae, and retracting the cannula thereby leaving the nuclear implant in the space. With the nuclear implant in a desired location, the method includes transferring the flexible material from the syringe to the body of the nuclear implant.

In yet another embodiment, the present invention provides a ready-to-use kit for positioning the implant between two intervertebral bodies.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "supported," and "coupled" and variations thereof are used broadly and encompass both direct and indirect connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

Figure 1A:
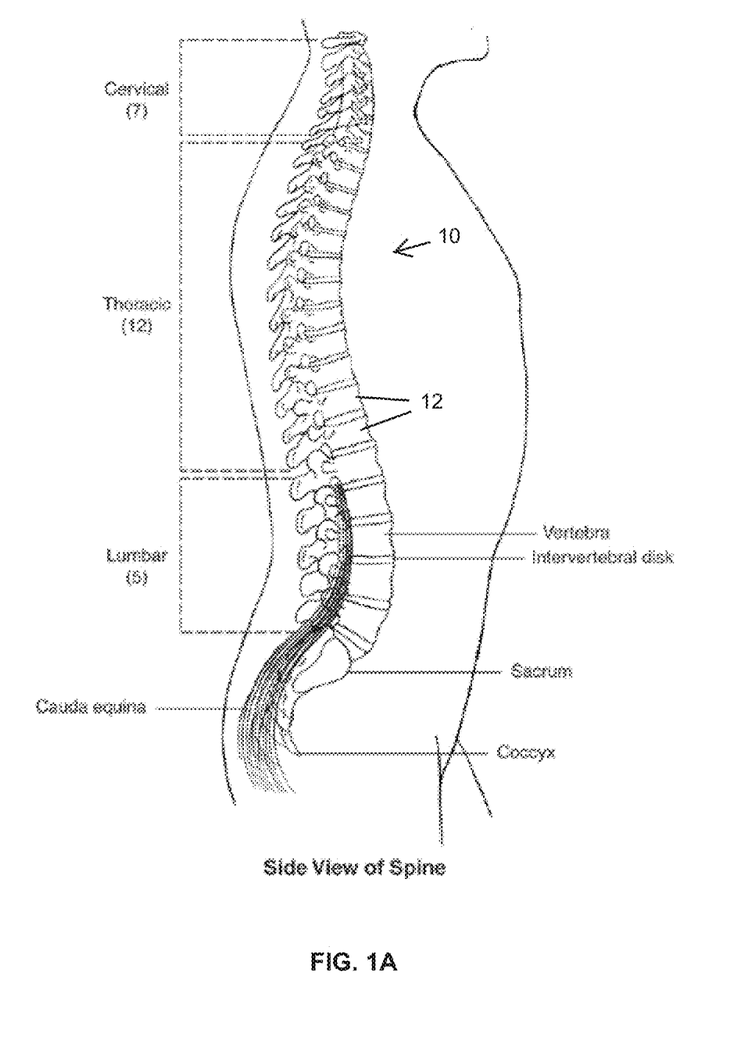
FIG. 1A is a side view of the human spine.
Figure 1B:
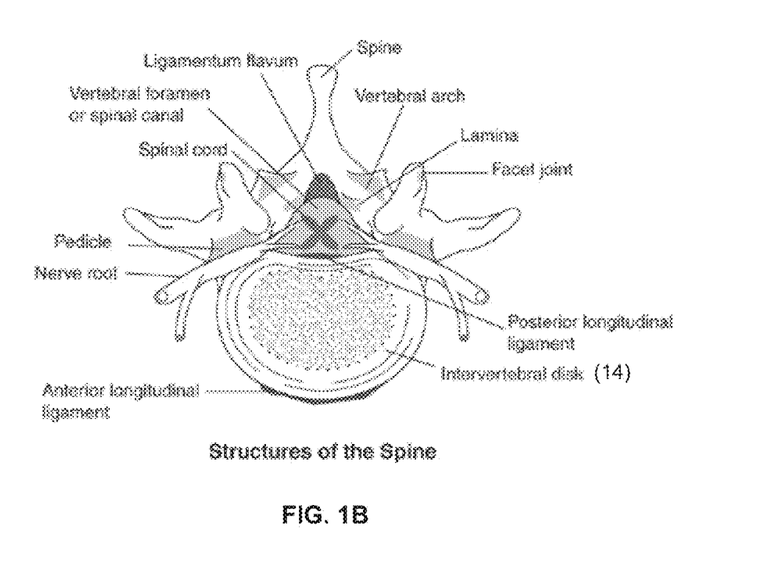
FIG. 1B is a top cross-sectional view of a portion of the human spine.
Figure 1C:
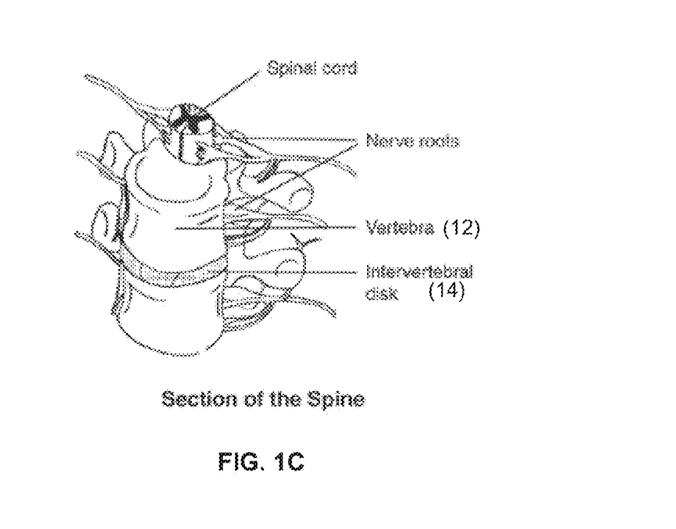
FIG. 1C is a perspective view of a portion of the human spine.
Figure 2:
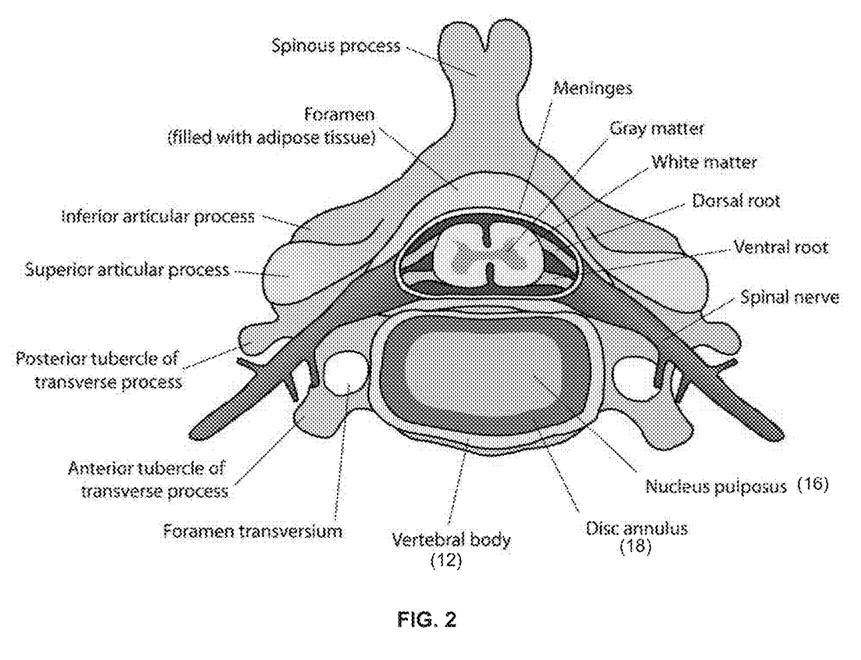
FIG. 2 is a top cross-sectional view of a portion of the human spine.
Figure 3:
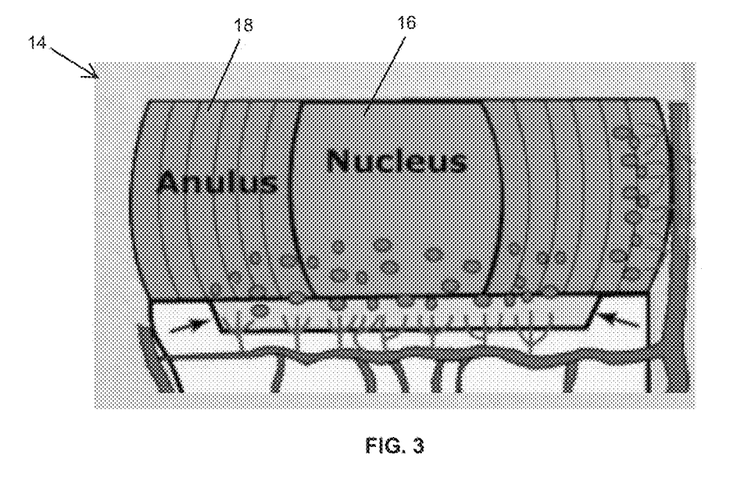
FIG. 3 is an enlarged view of an intervertebral disc.
Figure 4:
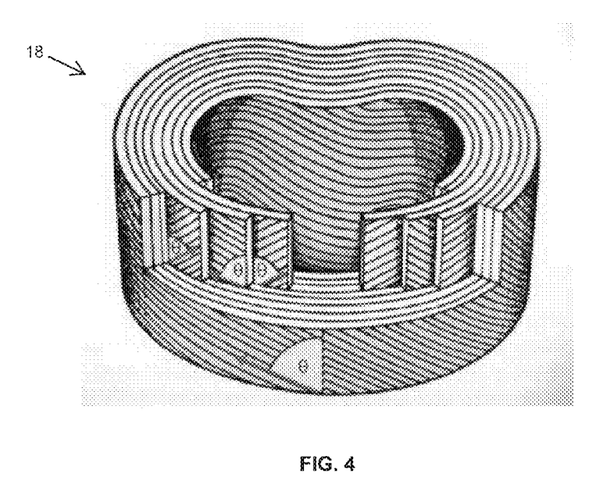
FIG. 4 is a perspective view of the collagen fiber orientation of an intervertebral disc.

FIG. 1A illustrates the human spine 10 while FIGS. 1B and 1C illustrate a portion of the spine in detail. As illustrated in FIGS. 1A-1C, the human spine 10 is made up of consecutively aligned vertebral bodies 12 (i.e., vertebrae). Adjacent vertebrae 12 are separated by an intervertebral disc 14. The discs are avascular, fibrocartilaginous structures that act as cushions or shock absorbers to protect the vertebrae 12 and spinal cord, in addition to other structures. With reference to FIGS. 2-3, each disc 14 includes a nucleus pulposus 16 that is enclosed within an annulus fibrosis 18. The annulus 18 is made up of collagen having an alternating fiber orientation as illustrated in FIG. 4. Under normal conditions, the nucleus pulposus 16 maintains the vertical structure of the annulus fibrosis 18 such that together, the nucleus 16 and the annulus 18 provide axial support to the spine 10.

Figure 5:
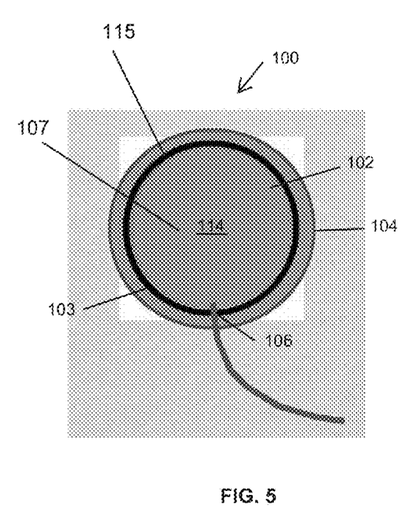
FIG. 5 is a top view of an implant according to an embodiment of the present invention.
Figure 6:
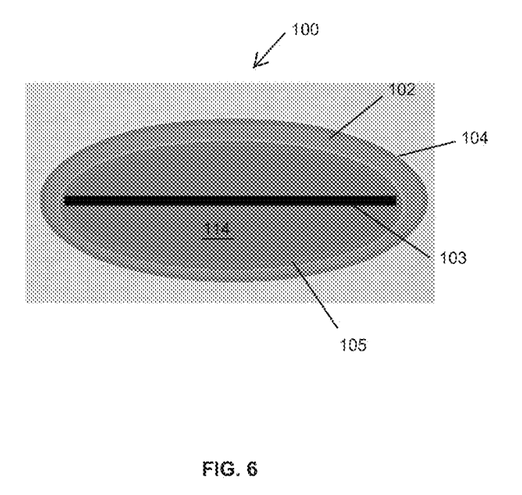
FIG. 6 is a side view of the implant illustrated in FIG. 5.

FIGS. 5-6 illustrate an implant 100 capable of being positioned within the space designated for the nucleus pulposus 16 of an intervertebral disc 14. When in use, the implant 100 replaces at least a portion of the nucleus pulposus 16. The implant 100 is a synthetic structure generally formed in the shape of a disc/ellipse (as illustrated in the figures) depending on viewing orientation, however other suitable shapes for the implant 100 are contemplated as well. The implant 100 includes a body 102 having an internal compartment 107 enclosed by an outer wall 104. The body 102 also includes a port 106 extending from an exterior of the body to the internal compartment 107. The implant 100 is flexible and deformable such that it can be inserted inside a cannula 108 in preparation for implantation. As such, the implant 100 has a first state 110 and a second state 112 discussed in further detail below with respect to FIGS. 7-9. The implant 100 receives and encloses a fluid or semi-fluid biological material 114.

In one construction of the implant 100, the body 102 of the implant 100 includes a nitinol endoskeleton 103 that extends at least partially about a perimeter 115 of the body 102. The endoskeleton 103 provides shape memory and a radio-opaque marker to aid in percutaneous, fluoroscopic-guided positioning of and access to the device 100. Both implant 100 and the material 114 are made of biocompatible materials. The outer wall 104 of the implant 100 comprises polytetrafluoroethylene (PTFE) to prevent a foreign body response by the patient's immune system. In addition, the material 114 is preferably a hydrogel, which is highly water absorbent, biologically inert and possesses mechanical behavior (i.e., flexibility) similar to that of natural tissue. In other constructions of the implant 100, the outer wall 104, the nitinol endoskeleton 103, inner wall 105, and the material 114 can have other suitable biocompatible materials that also prevent a foreign body response and also exhibit mechanical behavior similar to that of natural tissue.

Figure 7:
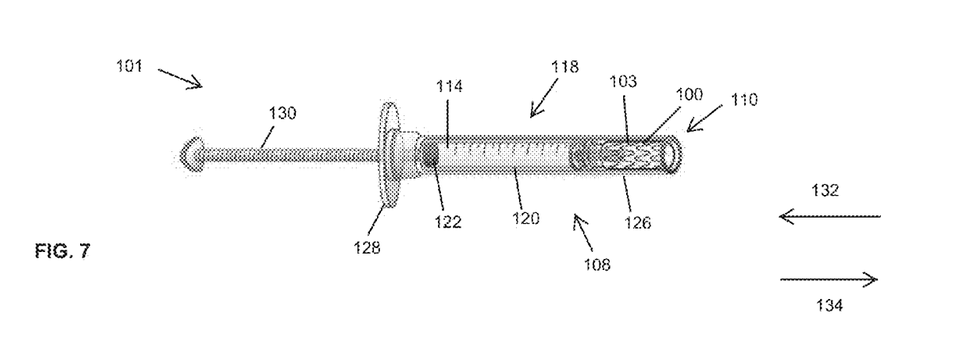
FIG. 7 is a side view of a medical instrument for disc restoration including an implant according to one embodiment of the invention where the implant is in a first state.
Figure 8:
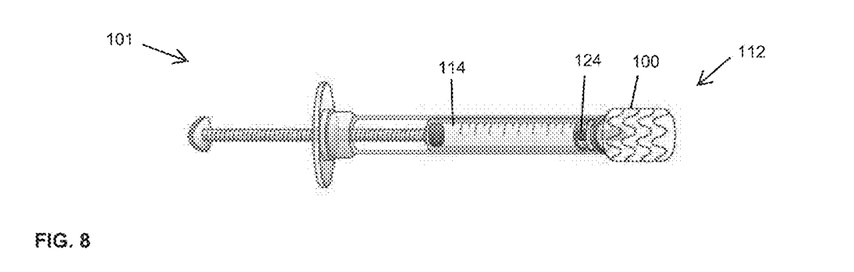
FIG. 8 is a side view of the medical instrument in FIG. 7 where the implant in a second state.
Figure 9:
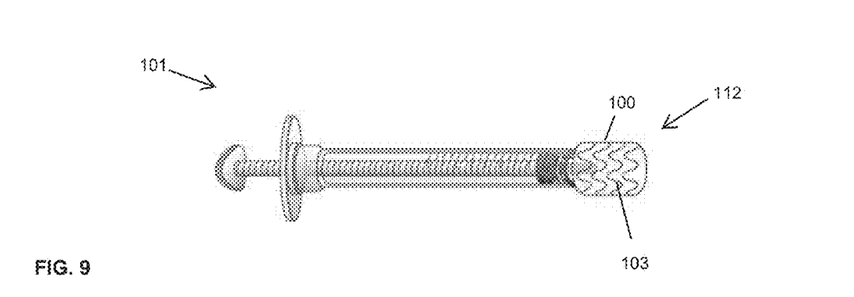
FIG. 9 is a side view of the medical instrument in FIG. 7 where the implant is in the second state and contains a flexible material.

With reference to FIGS. 7-9, the implant 100 is positioned in the intervertebral disc 14 (i.e., the space encompassed by the nucleus pulposus) with a device or instrument 101. The instrument 101 includes an assembly 118 capable of supporting the implant 100 and positioning the implant 100. The assembly 118 includes a tubular container 120 capable of holding the material 114 (or other suitable material), a plunger 122, and a conduit 124. The conduit 124 is coupled to the port 106 of the implant 100 such that the container 120 of the assembly 118 is in fluid communication with the body 102 of the implant 100. In one construction, the assembly 118 includes a luer-lock type syringe. The plunger 122 includes threads 130 and is rotatably actuated along the threads 130 to eject the contents of the container 120. The instrument 101 also includes the cannula 108, which at least partially or fully surrounds a portion of the container 120. The cannula 108 may also at last partially or fully surround a portion of the implant 100. The cannula 108 further includes an outer sheath 126 having a hub 128. The outer sheath 126 is configured to retract upon actuation to release or uncover the implant 100.

Prior to implantation, the assembly 118 is coupled to the implant 100 while it is in the first state 110, and both the assembly 118 and the implant 100 are housed within the cannula 108. While in this configuration, the container 120 of the assembly 118 contains the material 114, and the implant 100 is empty or partially empty. When the cannula 108 is inserted into the patient at the desired location, the implant 100 moves from the first state 110 to the second state 112, which is beyond a distal end 129 of the cannula 108. While the implant 100 is in the second state 112 and still coupled to the assembly 118, the material 114 is transferred from the container 120 of the assembly 118 into the body 102 of the implant 100 via the conduit 124 and the port 106.

To operate the instrument 101, the implant 100 is pre-mounted onto the assembly 118 such that the conduit 124 is coupled to the port 106 of the implant 100. The container 120 of the assembly 118 contains the material 114. The assembly 118 and the implant 100, which is in its first state 110, is inserted into the cannula 108 (as illustrated in FIG. 7). The cannula 108 is then inserted into and positioned at a desired location between two adjacent vertebral bodies 12. The cannula 108 further penetrates through the annulus fibrosis and into the space previously occupied by (or at least still partially occupied by) the nucleus pulposus. The cannula 108 is then rotatably retracted along the threads 130 of the plunger 122 in the direction of arrow 132, which releases the implant 100 from its first state 110 to its second state 112 (as illustrated in FIG. 8). The plunger 122 is then rotatably deployed in the direction of arrow 134, in order to transfer the material 114 from the container 120 of the assembly 118 through the conduit 124 and into the body 102 of the implant 100 (as illustrated in FIG. 9).

When the implant 100 is deployed to its second state 112, the device assumes the shape determined by the nitinol endoskeleton and thus, fits within the space previously occupied by the nucleus pulposus. Because the implant 100 includes some rigidity (but is yet still flexible), it maintains its shape and restores height of the annulus for improved structural integrity of the spine. This is in contrast to other implants that have no endoskeleton beyond that of the outer wall (such as in a balloon). The implant 100 is not a simple balloon, but rather a PTFE lined apparatus constrained in the XY plane by a nitinol ring. The size of the implant 100 is customized to the patient's anatomy based on pre-operative MR imaging. The XY constraint is important, as a simple balloon may not have as accurate a shape as desired. The filling of the implant 100 will then complete the shape of the implant 100 and specifically provide shape and support in the Z axis (cranial and caudal).

Figure 10:
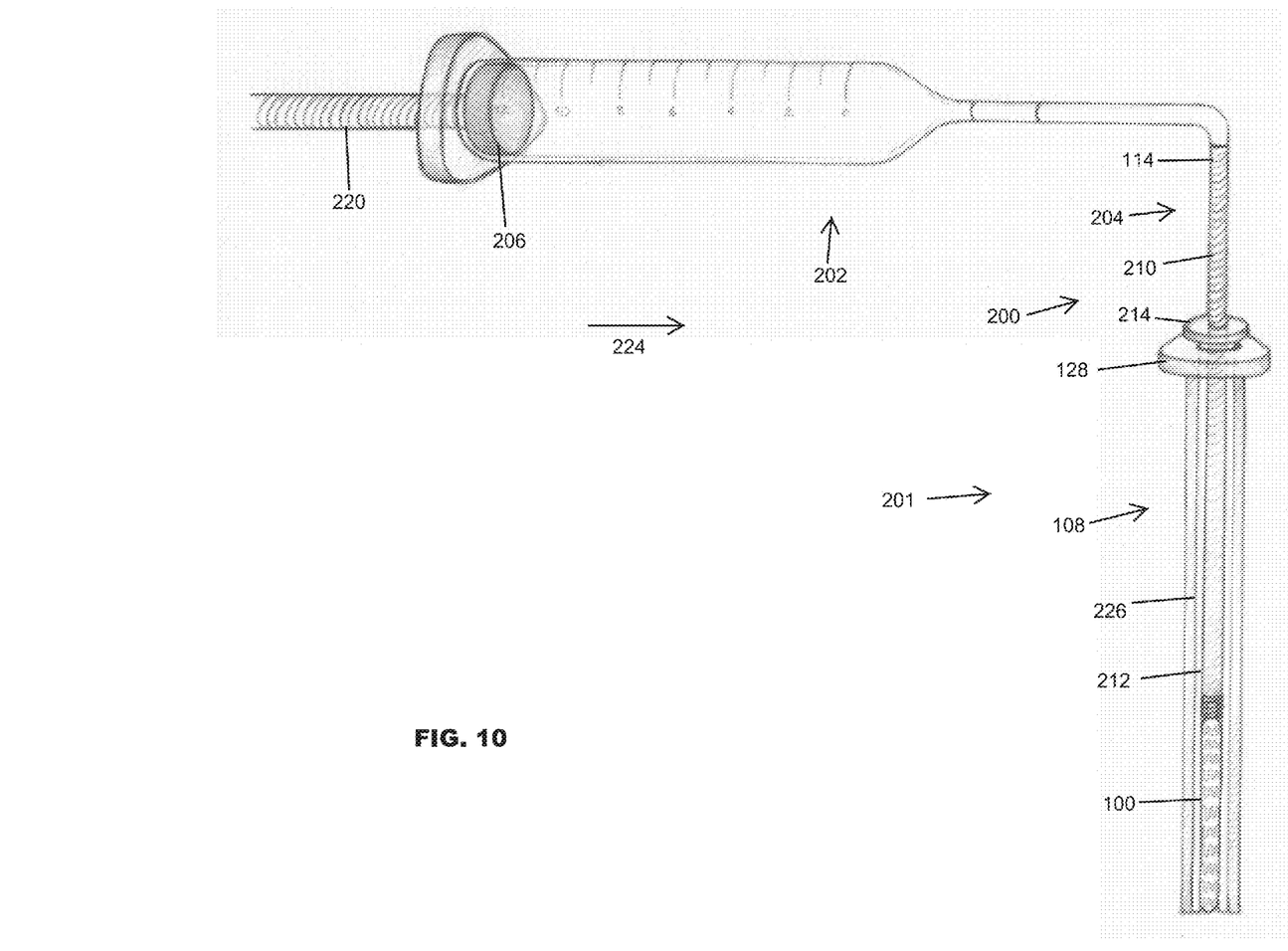
FIGS. 10-12 illustrate a medical instrument for repairing degenerating intervertebral discs according to another embodiment of the invention.
Figure 11:
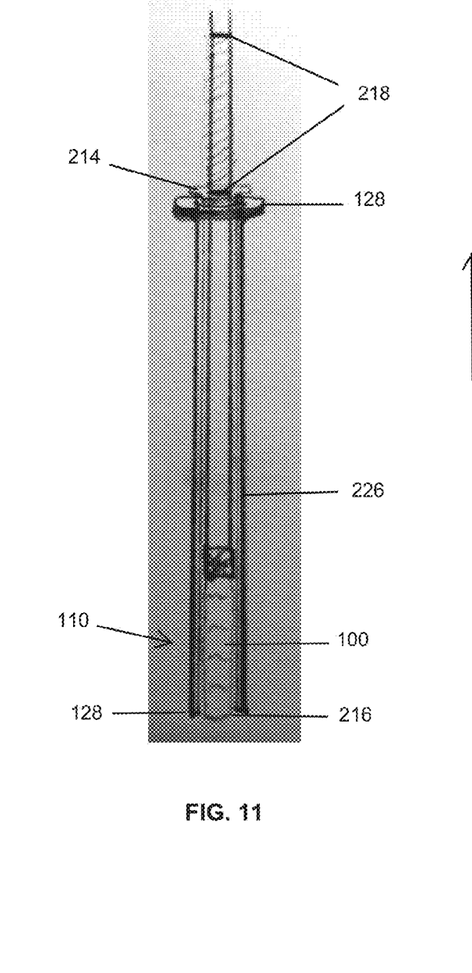
Figure 12:
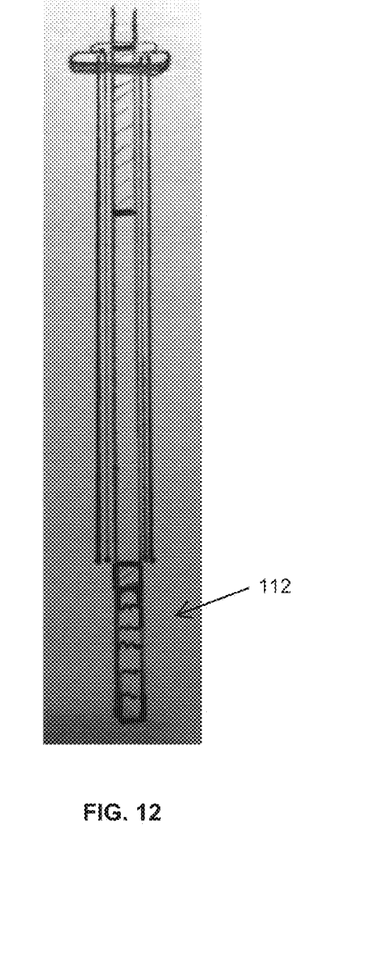
Figure 13:
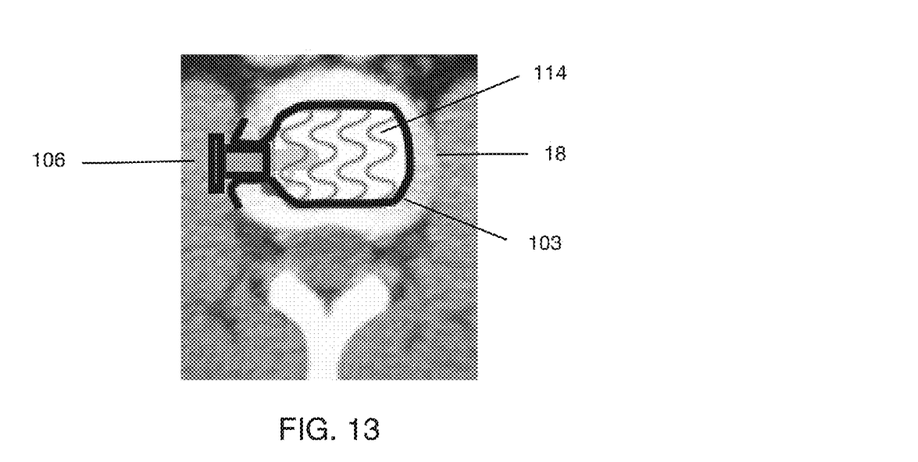
FIGS. 13-16 illustrate the implant shown in FIGS. 5-6 implanted between two intervertebral bodies of the spine.
Figures 14, 15:
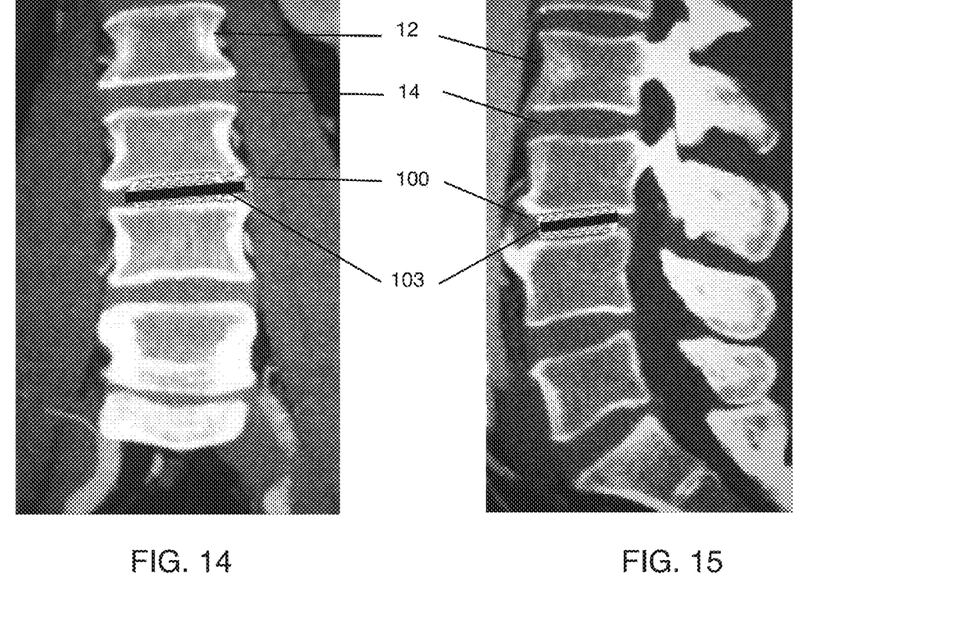

FIGS. 10-12 illustrate another construction of an instrument 201 used for positioning the implant 100. The instrument 201 includes an assembly 200 (e.g., a syringe) and the cannula 108. The assembly 200 is coupled to the implant 100 and includes a first portion 202, a second portion 204, and a plunger 206. The first portion 202 of the assembly 200 has a first diameter and the second portion 204 of the assembly 200 has a second diameter such that the second diameter is smaller than the first diameter. The second portion 204 includes a distal end 212 coupled to the port 106 of the implant 100 such that the first portion 202 of the assembly 200 is in fluid communication with the body 102 of the implant 100. In the illustrated embodiment, the second portion 204 is oriented at about a 90° angle with respect to the first portion 202. However, in other embodiments the first and second portions 202, 204 could be oriented at other suitable angles with respect to one another. The distal end 212 of the second portion 204 is received within the cannula 108. The hub 214 of the sheath 226 interconnects with the hub 128 of the access cannula 108, positioning the end of the implant 100 at end 216 with the distal end of the access cannula 108. The second portion 204 additionally includes deployment markers 218, which prevents improper deployment of the implant 100. The hub 128 of the access cannula 108, interconnects with the hub 214 of the sheath 226. The hub 128 of the access cannula 108 is then rotatably actuated along the threads 210 of the second portion 204 of the delivery instrument 200, effectively unsheathing the implant 100 within the confines of the annulus fibrosus 18. The assembly 200 is preferably a luer-lock syringe. The first portion 202 has a plunger 206 which includes threads 220 and is rotatably actuated along the threads 220 to eject the material 114 into the implant 100.

To operate the medical instrument 201, the implant 100 is pre-mounted onto the distal end 212 of the second portion 204 such that the second portion 204 is coupled to the port 106 of the implant 100. The first portion 202 and the second portion 204 of the assembly 200 contain the material 114. The cannula 108 is then inserted into and positioned at a desired location between two adjacent vertebral bodies 12. The access cannula 108 is then positioned within the nucleus pulposus 16, which is removed percutaneously using thermal ablation and mechanical extraction devices. The assembly 200 and the implant 100, which is in its first state 110, are inserted into the cannula 108. The hub 128 of the cannula 108 interconnects with a hub 214 of the sheath 226, which are then rotatably retracted along the threads 210 of the second portion 204 in the direction of arrow 222, which releases the implant 100 from its first state 110 to its second state 112. This mechanism of delivery allows for repositioning of the implant 100 by inverse rotatable actuation and resheathing of the implant 100 within the sheath 226 and cannula 108 to allow for intra-operative adjustments prior to final deployment in its second state 112 and filling of the implant 100. The plunger 206 is rotated in the direction of arrow 224 thereby transferring the material 114 from the first portion 202 and the second portion 204 of the assembly 200 into the body 102 of the implant 100.

Figure 16:
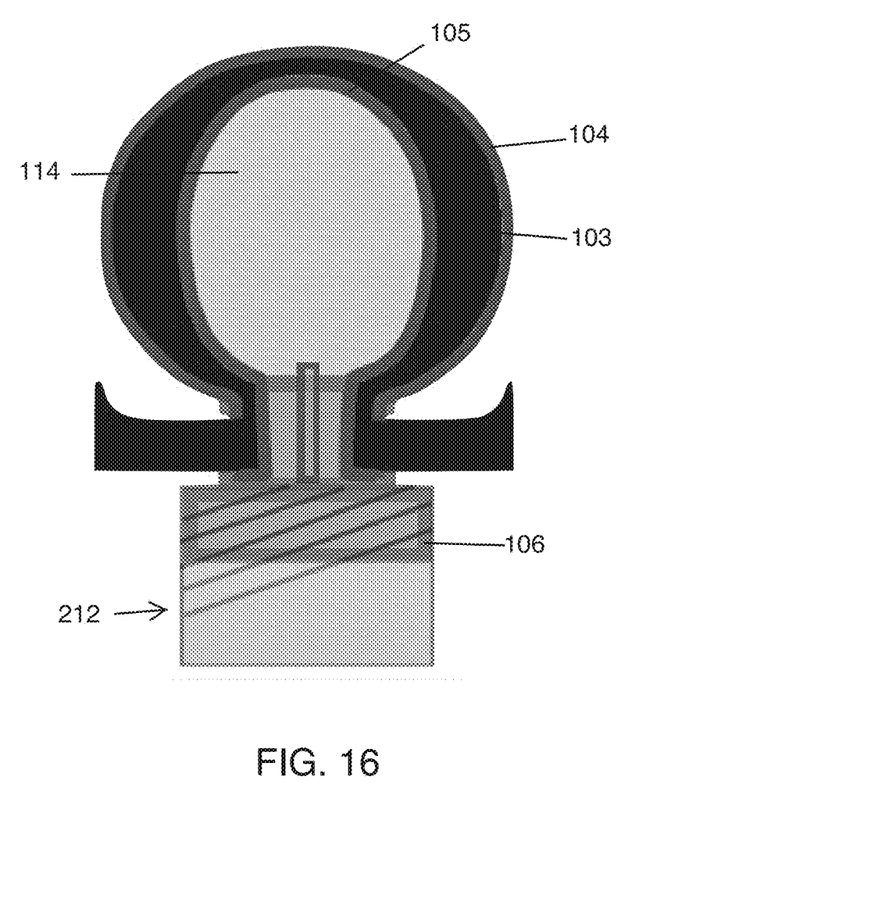

FIGS. 13-16 illustrate the implant 100 after it has been inserted into the space formerly occupied by the nucleus pulposus 16 of a degenerated intervertebral disc 14. The nitinol endoskeleton 103 includes an omega shape as illustrated in FIG. 16, however other suitable shapes may be employed. The omega-shaped nitinol endoskeleton 103 is integrated into the inner wall 105, outer wall 104 and the hub 106 of the implant 100. The short horizontal limbs of the omega shaped nitinol endoskeleton 103 anchor the implant 100 within the outer fibers of the annulus fibrosus 18 to reduce the risk of implant 100 migration. Further, the nucleus pulposus 16 has been removed and replaced by the implant 100 and the annulus fibrosis 18 restored. As such, the effects, symptoms and further degeneration of discs and the vertebral bodies have been mitigated without surgery or a hospital stay.

In the illustrated embodiment, the medical instrument 101, 201 includes an 8 gauge access cannula having an outer diameter of about 4.19 mm and an inner diameter of about 3.43 mm. Additionally, the syringe can be a dual diameter syringe capable of accommodating up to about 12 cc of hydrogel. It should be understood that the dimensions of the cannula, syringe assembly, and implant are for example only as these components are intended to be customizable based on an individual patient. For example, the gender and height of the patient are taken into account, as well as height restoration measurements and volumetric planning from a pre-operative MRI. Further, the location of the disc (i.e., disc level) is also considered and accounted for pre-operatively. These factors also participate in determining the volume of hydrogel that is used in the nucleus pulposus replacement.

Further embodiments of the invention include a medical instrument for retrieval and replacement and a cervical spine device.

The invention also includes a ready-to-use kit for positioning the implant 100 between two intervertebral bodies 12. In one example, the kit contents can include:
1. 18 gauge access needle
2. 0.035 inch super stiff J tip guidewire (40 cm long)
3. 8 gauge access cannula
4. Dilators (6,8,&10 Fr.)
5. RFA probe
6. High pressure balloon for disc distraction
7. Pre-mounted device/hydrogel syringe
8. Pre-mounted collagen plug Other components may also be included in the kit or less than all the components identified above can be included in the kit. Further, the kit can be configured to accommodate multiple sizes (variable dimensions and volumes for custom fit based on patient size, gender and disc level) as follows:

|    | AP    | ML    | CC    | NP VOLUME |
|----|-------|-------|-------|-----------|
| P1 | 20 mm | 30 mm | 6 mm  | 3.6 CC    |
| P2 | 20 mm | 30 mm | 8 mm  | 4.8 CC    |
| P3 | 25 mm | 35 mm | 8 mm  | 7.0 CC    |
| P4 | 25 mm | 35 mm | 10 mm | 8.8 CC    |
| P5 | 30 mm | 40 mm | 8 mm  | 9.6 CC    |
| P6 | 30 mm | 40 mm | 10 mm | 12 CC     |

What is claimed is:
1. A spinal implant comprising:
a body including an internal compartment enclosed by an outer wall, the body having an undeployed state and a deployed state; and a self-expanding, omega-shaped nitinol endoskeleton configured to support the body, the endoskeleton being configured to constrain the body in an XY plane and to allow the body to expand along a cranial-caudal plane perpendicular to the XY plane, the omega-shaped nitinol endoskeleton including integral projections configured to anchor the endoskeleton into an annulus fibrosus of a spinal disc after implantation by a device; and a hub connected to and extending outward from the body and removably coupleable to the device, the hub providing fluid communication with the internal compartment for delivery of biological fluid from the device.

2. The spinal implant of claim 1, wherein the body is deformable.

3. The spinal implant of claim 1, wherein the body is disc-shaped or ellipse-shaped.

4. The spinal implant of claim 1, wherein the body is configured to be positioned between adjacent spinal vertebrae in the deployed state.

5. The spinal implant of claim 1, wherein the device is configured to position the body between adjacent spinal vertebrae, the device including:
   a cannula,
   a container coupled to the cannula, the container including the biological fluid and having a first end and a second end,
   a plunger threadingly coupled to the first end of the container, and
   a conduit coupled to the second end of the container and the hub to thereby provide fluid communication between the container and the body to fill the body with the biological fluid.

6. The spinal implant of claim 5, wherein in the undeployed state:
   the hub is coupled to the conduit, while the body is compressed, and while the body is positioned within the cannula.

7. The spinal implant of claim 5, wherein in the deployed state:
   the body is expanded, and
   the body is filled with the biological fluid.

8. The spinal implant of claim 5, wherein the body is moved from the undeployed state to the deployed state by:
   rotatably retracting the cannula in a first direction along threads of the plunger thereby releasing the body from the cannula; and
   rotatably deploying the plunger in a second direction along the threads thereby transferring the fluid from the container to the body through the conduit.

9. The spinal implant of claim 1, wherein the biological fluid is a hydrogel.

10. The spinal implant of claim 1, wherein the body is configured to replace at least a portion of a nucleus pulposus of a vertebral disc.

11. The spinal implant of claim 1, wherein the nitinol endoskeleton further includes a radio-opaque marker.

12. A method of implanting the spinal implant of claim 1, using a device, the method comprising:
   coupling the implant of claim 10 to the device;
   positioning the implant between adjacent vertebrae; and
   transferring the biological fluid from the device to the implant thereby expanding the implant from the undeployed state to the deployed state such that the implant replaces at least a portion of a nucleus pulposus of an intervertebral disc.

13. The method of claim 12, wherein coupling the implant to the device includes removably coupling the hub of the implant to a conduit of the device, the conduit being fluidly coupled to a container containing the biological fluid.

14. The method of claim 13, wherein transferring the biological fluid from the device to the implant includes actuating a plunger that is threadingly coupled to the container such that a force of the plunger on the biological fluid moves the fluid from the container to the body of the implant through the conduit.

* * * * *